(12) United States Patent
Detolla et al.

(10) Patent No.: US 10,417,382 B1
(45) Date of Patent: Sep. 17, 2019

(54) METHODS, APPARATUSES, AND SYSTEMS FOR DERIVING AN EXPECTED EMERGENCY DEPARTMENT VISIT LEVEL

(71) Applicant: Optum, Inc., Minnetonka, MN (US)

(72) Inventors: Michael J. Detolla, Issaquah, WA (US); Shannon L. Weintraub, Woodinville, WA (US); Ernest Valente, Jr., San Rafael, CA (US)

(73) Assignee: Optum, Inc., Minnetonka, MN (US)

( * ) Notice: Subject to any disclaimer, the term of this patent is extended or adjusted under 35 U.S.C. 154(b) by 0 days.

(21) Appl. No.: 15/663,076

(22) Filed: Jul. 28, 2017

(51) Int. Cl.
*G06F 19/00* (2018.01)

(52) U.S. Cl.
CPC .................. *G06F 19/328* (2013.01)

(58) Field of Classification Search
USPC ........................................................ 705/2–4
See application file for complete search history.

(56) References Cited

U.S. PATENT DOCUMENTS

| | | | | |
|---|---|---|---|---|
| 5,359,509 A * | 10/1994 | Little | .................... | G06F 19/325 705/2 |
| 6,529,876 B1 * | 3/2003 | Dart | ....................... | G06Q 10/10 705/2 |
| 8,666,772 B2 * | 3/2014 | Kaniadakis | .......... | G06F 19/328 382/182 |
| 2006/0020492 A1 * | 1/2006 | Cousineau | ............ | G06F 17/278 705/2 |
| 2011/0246229 A1 * | 10/2011 | Pacha | .................... | G06F 19/328 705/2 |
| 2015/0039344 A1 * | 2/2015 | Kinney | ................. | G06F 19/322 705/3 |

OTHER PUBLICATIONS

Novitas Solutions Documentation Worksheet (Novitas Solutions, 1995, available online at https://www.novitas-solutions.com/webcenter/content /conn/UCM_Repository/uuid/dDocName:00004966).*
King, Mitchell S., Lisa Sharp, and Martin S. Lipsky. "Accuracy of CPT evaluation and management coding by family physicians." J Am Board Fam Pract 14.3 (2001): 184-192.*
3M Enhanced Ambulatory Patient Grouping System (brochure), 3M Health Information Systems (dated Nov. 2016) 4 pages.

* cited by examiner

*Primary Examiner* — Mark Holcomb
(74) *Attorney, Agent, or Firm* — Alston & Bird LLP

(57) ABSTRACT

Computer program products, methods, systems, apparatus, and computing entities for deriving an expected emergency department visit level are described. In one example embodiment, an example computing device receives a set of healthcare claims representing a patient's visit to an emergency department and extracts a set of treatment codes from the set of healthcare claims. The treatment codes represent services performed during the emergency department visit and the condition of the patient. The example computing device also derives a standard value, an extended value, and a patient complexity adjustment using the set of treatment codes, and determines the expected emergency department visit level using the standard value, the extended value, and the patient complexity adjustment.

11 Claims, 10 Drawing Sheets

| | A | B | C | D | E | F | G | |
|---|---|---|---|---|---|---|---|---|
| | # | PP ID | PSCA | Major Problem | Minor Problem | Problem Selector | RFV | ICD-10-CM Code |
| 1 | 1777 | 2991 | 3 | Wrist Pain - Swelling | Wrist Pain - Swelling | Wrist | M25.439 | M25.539 |
| 2 | 2522 | 814 | 2 | Laceration | Wrist Laceration | L | S61.512 | S61.522 |
| 3 | 2523 | 2437 | 2 | Laceration | Wrist Laceration | R | S61.511 | S61.521 |
| 4 | 2521 | 3051 | 2 | Laceration | Wrist Laceration | Wrist | S61.519 | S61.529 |
| 5 | 2464 | 1329 | 3 | Injury - Extremity (f) | Wrist Injury (f) | L | S69.92 | S69.92 S69.92XA |
| 6 | 2465 | 853 | 3 | Injury - Extremity (f) | Wrist Injury (f) | R | S69.91 | S69.91 S69.91XA |
| 7 | 2463 | 3106 | 3 | Injury - Extremity (f) | Wrist Injury (f) | Wrist | S69.90 | S69.90 |
| 8 | 2407 | 1681 | 4 | Injury - Extremity (c) | Wrist Injury (c) | L | S62.92 | S63.005 |
| 9 | 2408 | 1694 | 4 | Injury - Extremity (c) | Wrist Injury (c) | R | S62.91 | S63.004 |
| 10 | 2406 | 2983 | 4 | Injury - Extremity (c) | Wrist Injury (c) | Wrist | S69.90 | S69.90 |
| 11 | 2243 | 7562 | 2 | Wound Re-evaluation w/wo Suture/Staple Removal | Wound Re-evaluation w/wo Suture/Staple removal | Wound with(out) Suture/Staple removal | Z48.02 | Z09 Z48.00 Z48.817 Z48.89 |
| 12 | 1724 | 471 | 2 | Wound Infection (uncomplicated) | Wound Infection (uncomplicated) | Wound Infection (uncomplicated) | L08.89 | L08.9 L76.82 T81.4 |
| 13 | 1725 | 3257 | 2 | Wound Infection (uncomplicated) | Wound Infection (uncomplicated) | Wound Infection (uncomplicated) | L08.89 | L08.9 L76.82 T81.4 |
| 14 | 1722 | 5291 | 4 | Wound Infection (complicated) | Wound Infection (complicated) | Wound Infection (complicated) | L08.89 | L08.9 L76.82 T81.4 |
| 15 | 1723 | 5292 | 4 | Wound Infection (complicated) | Wound Infection (complicated) | Wound Infection (complicated) | L08.89 | L08.9 L76.82 T81.4 |
| 16 | 2242 | 6848 | 2 | Wound Drain Evaluation | Wound Drain Evaluation | Wound Drain Evaluation | Z48.03 | |
| 17 | 1040 | 67 | 5 | Wheezing | Wheezing | Wheezing | R06.2 | |
| 18 | 1041 | 669 | 4 | Wheezing | Wheezing | Wheezing | R06.2 | |
| 19 | 1670 | 3634 | 4 | Weight Loss and Anorexia | Weight Loss and Anorexia | Weight Loss & Anorexia | R63.0 | R63.4 |
| 20 | 1667 | 3229 | 5 | Weakness | Weakness | Weakness | R53.1 | |
| 21 | 1668 | 453 | 5 | Weakness | Weakness | Weakness | R53.1 | |
| 22 | 1669 | 4996 | 5 | Weakness | Weakness | Weakness | R53.1 | |
| 23 | 1595 | 5435 | 4 | Nausea/Vomiting | Vomiting, Pregnant | Vomiting - Pregnant | O21.0 | O21.8 O21.9 |
| 24 | 1593 | 5434 | 4 | Nausea/Vomiting | Vomiting | Vomiting | R11.10 | R11.2 |
| 25 | 1601 | 1474 | 4 | Vomiting | Vomiting | Vomiting | P92.0 | P92.09 R11.10 R11.11 |
| 26 | 1480 | 3078 | 4 | Eye | Vision Change | Vision Change | H53.8 | H53.9 |
| 27 | 1449 | 5346 | 3 | Ear | Vertigo - Recurrent | Vertigo - Recurrent | R42 | |
| 28 | 1539 | 1032 | 4 | Bite or Sting | Venomous Snake Bite | Snake Bite - Venomous | T63.001 | T63.004 |

FIG. 4A

| # | Problem Name | Problem Selector | ID | PSCA | M | F | < 8 wk | < 24 wk | < 24 mo | < 7 yr | < 12 yr | < 17 yr | < 40 yr | < 55 yr | < 75 yr | 75 + yr | Note |
|---|---|---|---|---|---|---|---|---|---|---|---|---|---|---|---|---|---|
| 19 | Diagnostic Test Pregnancy Test | Test - Pregnancy | 7,272 | 1 | | • | | | | | | • | • | • | • | | For an asymptomatic woman requesting a pregnancy test, if symptomatic choose a problem reflecting the symptoms. |
| 20 | Tobacco Cessation Counseling | Tobacco Cessation Counseling | 5,181 | 0 | • | • | | | | | | • | • | • | • | • | |
| 1000 | CARDIORESPERITORY | CARDIORESPERITORY | 25 | | • | • | • | • | • | • | • | • | • | • | • | • | Includes problems related to the cardiovascular or respiratory system, does not include upper respiratory infections or foreign bodies in the throat (see EENT/DENTAL-upper resperitory infection or EENT/DENTAL-foreign body-throat) |
| 1001 | ALTE (apparent life threatening event) | ALTE | 7,887 | 5 | • | • | • | • | • | | | | | | | | ALTE is sudden occurrence of stopped breathing, skin color change, muscle tone decrease, coughing or gagging that appear to be life threatening. |
| 1002 | Apnea - Pediatric | Apnea - Pediatric | 2,672 | 5 | • | • | • | • | • | | | | | | | | Episode of cessation of respiratory air flow. |
| 1003 | Apnea Episode - Adult | Apnea Episode - Adult | 5,186 | 4 | • | • | | | | | | • | • | • | • | • | Use for short apnea episode without other significant clinical symptoms. |
| 1004 | Cardiac and/or Resperitory Arrest | Arrest | 29 | 5 | • | • | | | | | | • | • | • | • | • | Complete cessation of resperitory airflow. May also include pulselessness and cessation of cardiac rythm. |
| 1005 | Cardiac and/or Resperitory Arrest | Arrest | 1,295 | 5 | • | • | • | • | • | • | • | | | | | | Complete cessation of resperitory airflow. May also include pulselessness and cessation of cardiac rythm. |

FIG. 4B

|   | A | B | C | D |
|---|---|---|---|---|
|   | Extended Value Category | cpt-code | Description | long-description |
| 1 | Lab Orders | 61070 | PNXR SHUNT TUBING/RSVR ASPIR/NJX | Puncture of shunt tubing or resivoir for aspiration or injection procedure |
| 2 | Lab Orders | 62270 | SPI PNXR LMBR DX | Spinal puncture, lumbar, diagnostic |
| 3 | CT/MRI/Ultrasound | 62284 | INJECTION PROCEDURE MYELOGRAPHY/CT SPINAL | Injection procedure for myelography and/or computed tomography, lumbar (other than C1-C2 and posterior fossa) |
| 4 | EKG/RT/Other Diagnostic Orders | 62302 | MYELOGRAPHY LUMBAR INJECTION | Myelography via lumbar injection, including radiological supervision and interpretation; cervical |
| 5 | EKG/RT/Other Diagnostic Orders | 62303 | MYELOGRAPHY LUMBAR INJECTION | Myelography via lumbar injection, including radiological supervision and interpretation; thoracic |
| 6 | EKG/RT/Other Diagnostic Orders | 62304 | MYELOGRAPHY LUMBAR INJECTION | Myelography via lumbar injection, including radiological supervision and interpretation; lumbosacral |
| 7 | EKG/RT/Other Diagnostic Orders | 62305 | MYELOGRAPHY LUMBAR INJECTION | Myelography via lumbar injection, including radiological supervision and interpretation; 2 or more regions (eg, lumbar/thoracic, cervical/thoracic, lumbar/cervical, lumbar/thoracic/cervical) |
| 8 | Lab Orders | 67700 | BLEPHORATOMY DRG ABSC EYELID | Blepharotomy, drainage of abscess, eyelid |
| 9 | Lab Orders | 69000 | DRG XTRNL EAR ABSC/HMTMA SMPL | Drainage external ear, abscess or hematoma; simple |
| 10 | Lab Orders | 69005 | DRG XTRNL EAR ABSC/HMTMA COMP | Drainage external ear, abscess or hematoma; complicated |
| 11 | Lab Orders | 69020 | DRG XTRNL AUD CANAL ABSC | Drainage external auditory canal, abscess |
| 12 | Lab Orders | 69100 | BX XTRNL EAR | Biopsy external ear |
| 13 | Lab Orders | 69105 | BX XTRNL AUD CANAL | Biopsy external auditory canal |
| 14 | Xray - Plain Film Orders | 70010 | MYELOGRAPHY POST FOSSA RS&I | Myelography, posterior fossa, radiological supervision and interpretation |
| 15 | EKG/RT/Other Diagnostic Orders | 70015 | CISTNG POSITIVE CNTRST RS&I | Cisternography, positive contrast, radiological supervision and interpretation |
| 16 | Xray - Plain Film Orders | 70030 | RADEX EYE DETCJ FB | Radiologic examination, eye, for detection of foreign body |
| 17 | Xray - Plain Film Orders | 70100 | RADEX MNDBL PRTL < 4 VIEWS | Radiologic examination, mandible, partial, less than 4 views |
| 18 | Xray - Plain Film Orders | 70110 | RADEX MNDBL COMPL MINIMUM 4 VIEWS | Radiologic examination, mandible; complete, minimum of 4 views |
| 19 | Xray - Plain Film Orders | 70120 | RADEX MASTOIDS < 3 VIEWS PR SIDE | Radiologic examination, mastoids; less than 3 views per side |
| 20 | Xray - Plain Film Orders | 70130 | RADEX MASTOIDS COMPL MINIMUM 3 VIEWS PR SIDE | Radiologic examination, mastoids; complete, minimum of 3 views per side |
| 21 | Xray - Plain Film Orders | 70320 | RADEX TEETH COMPL FULL MOUTH | Radiologic examination, teeth; complete, full mouth |
| 22 | Xray - Plain Film Orders | 70328 | RADEX TMPRMAND JT OPN&CLSD MOUTH UNI | Radiologic examination, temporomandibular joint, open and closed mouth; unilateral |
| 23 | Xray - Plain Film Orders | 70330 | RADEX TMPRMAND JT OPN&CLSD MOUTH BI | Radiologic examination, temporomandibular joint, open and closed mouth; bilateral |
| 24 | Xray - Plain Film Orders | 70332 | TMPRMAND JT ARTHG RS&I | Temporomandibular joint arthrography, radiological supervision and interpretation |
| 25 | CT/MRI/Ultrasound | 70336 | MRI TMPRMAND JT | Magnetic resonance (eg, proton) imaging, temporomandibular joint(s) |
| 26 | CT/MRI/Ultrasound | 70450 | CT HEAD/BRN C-MATRL | Computed tomography, head or brain; without contrast material |
| 27 | CT/MRI/Ultrasound | 70460 | CT HEAD/BRN C+MATRL | Computed tomography, head or brain; with contrast material(s) |
| 28 | CT/MRI/Ultrasound | 70470 | CT HEAD/BRN C-/C+ | Computed tomography, head or brain; without contrast material, followed by contrast material(s) and further sections |
| 29 | CT/MRI/Ultrasound | 70480 | CT ORBIT SELLA/POST FOSSA/EAR C-MATRL | Computed tomography, orbit, sella, or posterior fossa or outer, middle, or inner ear; without contrast material |
| 30 | CT/MRI/Ultrasound | 70481 | CT ORBIT SELLA/POST FOSSA/EAR C+MATRL | Computed tomography, orbit, sella, or posterior fossa or outer, middle, or inner ear; with contrast material(s) |

FIG. 5

| | A | B | C |
|---|---|---|---|
| | ICD Code | Comp Pts | ICD Title |
| 1 | R45850 | 500 | Homicidal ideations |
| 2 | F6389 | 500 | Other impulse disorders |
| 3 | T5912XA | 433 | Toxic effect of carbon monoxide from utility gas, intentional self-harm, initial encounter |
| 4 | T5492XA | 433 | Toxic effect of unspecified corrosive substance, intentional self-harm, initial encounter |
| 5 | T43504A | 310 | Poisoning by unspecified antipsychotics and neuroleptics, undetermined, initial encounter |
| 6 | T43501A | 310 | Poisoning by unspecified antipsychotics and neuroleptics, accidental (unintentional), initial encounter |
| 7 | F10120 | 287 | Alcohol abuse with intoxication, uncomplicated |
| 8 | F349 | 286 | Persistant mood [affective] disorder, unspecified |
| 9 | W5532XA | 231 | Struck by other hoof stock, initial encounter |
| 10 | F6812 | 225 | Factitious disorder with predominantly physical signs and symptoms |
| 11 | F6811 | 225 | Factitious disorder with predominantly psychological signs and symptoms |
| 12 | G40901 | 189 | Epilepsy, unspecified, not intractable, with status epilepticus |
| 13 | G4089 | 189 | Other seizures |
| 14 | O161 | 133 | Unspecified maternal hypertension, first trimester |
| 15 | O159 | 133 | Eclampsia, unspecified as to time period |
| 16 | T402X5A | 104 | Adverse effect of other opioids, initial encounter |
| 17 | T3995XA | 104 | Adverse effect of unspecified nonopioid analgesic, antipyretic and antirheumatic, initial encounter |
| 18 | T398X5A | 104 | Adverse effect of other nonopioid analgesics and antipyretics, not elsewhere classified, initial encounter |
| 19 | T394X5A | 104 | Adverse effect of antirheumatics, not elsewhere classified, initial encounter |
| 20 | S91214A | 76 | Laceration without foreign body of right lesser toe(s) with damage to nail, initial encounter |
| 21 | S91212A | 76 | Laceration without foreign body of left great toe with damage to nail, initial encounter |
| 22 | S91211A | 76 | Laceration without foreign body of right great toe with damage to nail, initial encounter |
| 23 | S91209A | 76 | Unspecified open wound of unspecified toe(s) with damage to nail, initial encounter |
| 24 | C240 | 47 | Malignant neoplasm of extrahepatic bile duct |
| 25 | C23 | 47 | Malignant neoplasm of gallbladder |
| 26 | C179 | 47 | Malignant neoplasm of small intestine, unspecified |
| 27 | Z8547 | 36 | Personal history of malignant neoplasm of testis |
| 28 | C6292 | 36 | Malignant neoplasm of left testis, unspecified whether descended or undescended |
| 29 | C6291 | 36 | Malignant neoplasm of right testis, unspecified whether descended or undescended |
| 30 | G0489 | 31 | Other myelitis |
| 31 | G0481 | 31 | Other encephalitis and encephalomyelitis |
| 32 | R6521 | 27 | Severe sepsis with septic shock |
| 33 | R579 | 27 | Shock, unspecified |
| 34 | C4331 | 22 | Malignant melanoma of nose |
| 35 | C4322 | 22 | Malignant melanoma of left ear and external auricular canal |

FIG. 6

METHODS, APPARATUSES, AND SYSTEMS FOR DERIVING AN EXPECTED EMERGENCY DEPARTMENT VISIT LEVEL

TECHNOLOGICAL FIELD

Example embodiments of the present invention relate generally to healthcare claim coding and, more particularly, to methods and apparatuses that derive an adjusted or expected emergency department visit level.

BACKGROUND

The inventors have discovered limitations with existing computerized processing of healthcare insurance claims including the identification of over-claimed or overcharged healthcare insurance claims. Through applied effort, ingenuity, and innovation, the inventors have solved many of these identified limitations by developing a solution that is embodied by the present invention and described in detail below.

SUMMARY

With the increasing cost of healthcare and healthcare related expenses there is an increasing drive to ensure that healthcare is paid for in a consistent and verified manner. For example, there may be institutional pressures to overcode (i.e., classify medical treatment as more severe or serious than it really is), which allows a healthcare provider to collect a larger payment for the medical treatment of a patient. Correcting this overcoding is important to healthcare claims payers, especially institutional payers such as insurance companies and the Centers for Medicare and Medicaid services (CMS), which pay for large amounts of healthcare expenses, and for whom cost savings in any level of healthcare service can result in large savings. The overcoding and subsequent overcharging of medical treatment is generally kept in check by strict coding guidelines maintained by CMS and AMA (American Medical Association) for most patient procedures and treatment. However, one area of claim coding that has less stringent guidelines is outpatient emergency department facility visit level evaluation and management (E/M) coding. In general, E/M coding classifies services into a level between 1 and 5 that are meant to be tied to resource usage of the emergency department facility. E/M coding thus provides compensation to the emergency department facility for the volume and intensity of the resources used that the healthcare facility is not otherwise compensated for in other ways (e.g., through the billing of lab tests or the like). In general, each emergency department facility is responsible for creating or adopting a set of guidelines, methods, and/or algorithms for E/M coding and is also required to apply its guidelines consistently. However, the flexibility of the E/M coding guidelines has led to a patchwork of national and ad hoc guidelines for E/M coding that has produced inconsistent and in many cases overcoded claims across different emergency department facilities.

Indeed, payers like insurance companies and CMS have seen consistently increasing coding levels for emergency department visit levels despite not seeing a corresponding increase in the level of intensity required to treat patients. Thus, payers need a method to independently classify or code the E/M treatment which can be used to verify that the coded claims received from an emergency department facility actually reflect the acuity or intensity of each patient's condition and treatment and accurately reflect the resource usage of the facility that treated the patient's condition. Due to the large number of individual codes used to code claims and the large number of claims submitted to payers each day, manual examination of each of the submitted sets of claims for patient treatment would be impossible without large amounts of capital and labor that would itself introduce costs eliminating any cost savings a payer may see in correcting the coding of the overcoded claim sets. Moreover, human fallibility ensures that even the best managed staff would not be able to operate entirely consistently, and in any event, would not be able to guarantee an evaluation of every claim in near real time, and the introduction of human error and unreliability would further undercut the value of a human solution to this problem.

As described herein, the inventors have developed a system and method for receiving and verifying that the claimed treatment codes from emergency departments accurately reflects the treatment (e.g. facility resource usages and intensity) provided to the patient by utilizing treatment codes that are highly standardized to derive an expected emergency department visit level (EEDVL) code.

Accordingly, example methods, apparatuses, and computer program products described herein are designed to receive a set of healthcare claims for a patient's visit to an emergency department; extract, from the set of healthcare claims, a set of treatment codes representing services performed during the emergency department visit and the condition of the patient; derive, using the set of treatment codes, a standard value, an extended value, and a patient complexity adjustment; and determine the EEDVL using the standard value, the extended value, and the patient complexity adjustment.

In a first embodiment, a computer implemented method for deriving an expected emergency department visit level (EEDVL) is provided. The method comprises receiving, by communication circuitry of a computing device, a set of healthcare claims for a patient's visit to an emergency department and extracting, by a claims evaluator module of the computing device and from the set of healthcare claims, a set of treatment codes representing services performed during the emergency department visit and the condition of the patient. The method also comprises deriving, by an EEDVL module of the computing device and using the set of treatment codes, a standard value, an extended value, and a patient complexity adjustment, and determining the EEDVL by the EEDVL module of the computing device and using the standard value, the extended value, and the patient complexity adjustment.

In some embodiments, deriving the standard value also comprises identifying, by the EEDVL module of the computing device and from the set of treatment codes, one or more reasons for the patient's visit, determining, by the EEDVL module of the computing device and from a standard value database, a patient complexity adjustment (PSCA) score for each of the one or more reasons for the patient's visit, and deriving the standard value by the EEDVL module of the computing device and from the PSCA score.

In some embodiments, deriving the extended value comprises identifying, by the EEDVL module of the computing device and from the set of treatment codes, one or more resource utilization codes for the patient visit, determining, by the EEDVL module of the computing device and from an extended value database, an extended value score for each of the one or more resource utilization codes, and deriving the extended value by the EEDVL module of the computing device and the extended value score.

In some embodiments, deriving the extended value comprises summing the extended value scores for the one or more resource utilization codes.

In some embodiments, deriving the patient complexity adjustment comprises identifying, by the EEDVL module of the computing device and from the set of treatment codes, one or more secondary codes for the patient visit, determining, by the EEDVL module of the computing device and from a patient complexity adjustment database, a secondary score from the one or more secondary codes, and deriving the patient complexity adjustment by the EEDVL module of the computing device and from the secondary score.

In some embodiments, deriving the EEDVL comprises generating a final score by the EEDVL module of the computing device and based on the standard value, the extended value, and the patient complexity adjustment, and determining the EEDVL by the EEDVL module of the computing device and using the final score and a threshold table, wherein the threshold table comprises a set of threshold ranges corresponding to a set of emergency department visit levels, wherein the final score is within a particular threshold range of the set of threshold ranges, and wherein the EEDVL comprises the emergency department visit level corresponding to the particular threshold range.

In some embodiments, the computer implemented method further comprises providing, by the communication circuitry of the computing device, a notification comprising the EEDVL to a claim source.

In some embodiments, the computer implemented method further comprises identifying, by the claims evaluator module of the computing device and from the set of healthcare claims, a claimed emergency department visit level (CEDVL), and comparing, by the claims evaluator module of the computing device, the CEDVL with the EEDVL to determine whether the CEDVL comprises a higher or lower level than the EEDVL.

In some embodiments, in an instance in which the CEDVL comprises a higher or lower level than the EEDVL, the method further comprises providing, by the communication circuitry of the computing device, the notification to a claim source, wherein the notification comprises one or more of: a notification that the CEDVL is higher or lower than the EEDVL, or a notification the EEDVL will be used in a claims payout instead of the CEDVL.

In another embodiment, an apparatus for deriving an expected emergency department visit level (EEDVL) is provided. The apparatus comprising communication circuitry configured to receive a set of healthcare claims for a patient's visit to an emergency department. The apparatus also comprises a claims evaluator module configured to extract, from the set of healthcare claims, a set of treatment codes representing services performed during the emergency department visit and the condition of the patient. The apparatus also comprising an EEDVL module configured to derive, using the set of treatment codes, a standard value, an extended value, and a patient complexity adjustment, and determine, using the standard value, the extended value, and the patient complexity adjustment, the EEDVL.

In some embodiments, in order to derive the standard value the EEDVL module is further configured to identify, from the set of treatment codes, one or more reasons for the patient's visit, determine, from a standard value database, a patient complexity adjustment (PSCA) score for each of the one or more reasons for the patient's visit, and derive the standard value from the PSCA score.

In some embodiments, in order to derive the extended value the EEDVL module is further configured to identify, from the set of treatment codes, one or more resource utilization codes for the patient visit, determine from an extended value database, an extended value score for each of the one or more resource utilization codes, and derive from the extended value scores, the extended value.

In some embodiments, in order to derive the extended value the EEDVL module is further configured to sum the extended value scores for the one or more resource utilization codes.

In some embodiments, in order to derive the patient complexity adjustment the EEDVL module is further configured to identify, from the set of treatment codes, one or more secondary codes for the patient visit, determine, from a patient complexity adjustment database, a secondary score from the one or more secondary codes, and derive, from the secondary score, the patient complexity adjustment.

In some embodiments, in order to derive the EEDVL the EEDVL module is further configured to generate a final score based on the standard value, the extended value, and the patient complexity adjustment, and determine the EEDVL using the final score and a threshold table, wherein the threshold table comprises a set of thresholds ranges corresponding to a set of emergency department visit levels, wherein the final score is within a particular threshold range of the set of threshold ranges, and wherein the EEDVL comprises the emergency department visit level corresponding to the particular threshold range.

In some embodiments, the communication circuitry is further configured to provide a notification to a claim source comprising the EEDVL.

In some embodiments, the claims evaluator module is further configured to identify from the set of healthcare claims, a claimed emergency department visit level (CEDVL), and compare the CEDVL with the EEDVL to determine whether the CEDVL comprises a higher or lower level than the EEDVL.

In some embodiments, in an instance in which the CEDVL comprises a higher or lower level than the EEDVL, the communication circuitry is further configured to provide the notification to the claim source, wherein the notification comprises one or more of: a notification that the CEDVL is higher or lower than the EEDVL, or a notification the EEDVL will be used in a claims payout instead of the CEDVL.

In another example embodiment, a non-transitory computer-readable storage medium for healthcare provider network assessment is provided. The non-transitory computer-readable storage medium storing program code instructions that, when executed, cause a computing device to receive a set of healthcare claims for a patient's visit to an emergency department, extract, from the set of healthcare claims, a set of treatment codes representing services performed during the emergency department visit and the condition of the patient, derive, using the set of treatment codes, a standard value, an extended value, and a patient complexity adjustment, and determine the EEDVL using the standard value, the extended value, and the patient complexity adjustment.

In some embodiments, the program code instructions, when executed, further cause the computing device to: identify, from the set of treatment codes, one or more reasons for the patient's visit; determine, from a standard value database, a patient complexity adjustment (PSCA) score for each of the one or more reasons for the patient's visit; derive the standard value from the PSCA scores, identify, from the set of treatment codes, one or more resource utilization codes for the patient visit; determine from an extended value database, an extended value score for each of the one or more resource utilization codes; derive from the extended value scores, the extended value, identify, from the set of treatment codes, one or more secondary codes for the patient visit; determine, from a patient complexity adjustment database, a secondary score from the one or more secondary codes, derive, from the secondary score, the patient complexity adjustment; generate a final score based on the standard value, the extended value, and the patient complexity adjustment; and determine the EEDVL using the final score and a threshold table, wherein the threshold table comprises a set of thresholds ranges corresponding to a set of emergency department visit levels, wherein the final score is within a particular threshold range of the set of threshold ranges, and wherein the EEDVL comprises the emergency department visit level corresponding to the particular threshold range.

The above summary is provided merely for purposes of summarizing some example embodiments to provide a basic understanding of some aspects of the invention. Accordingly, it will be appreciated that the above described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Figure 1:
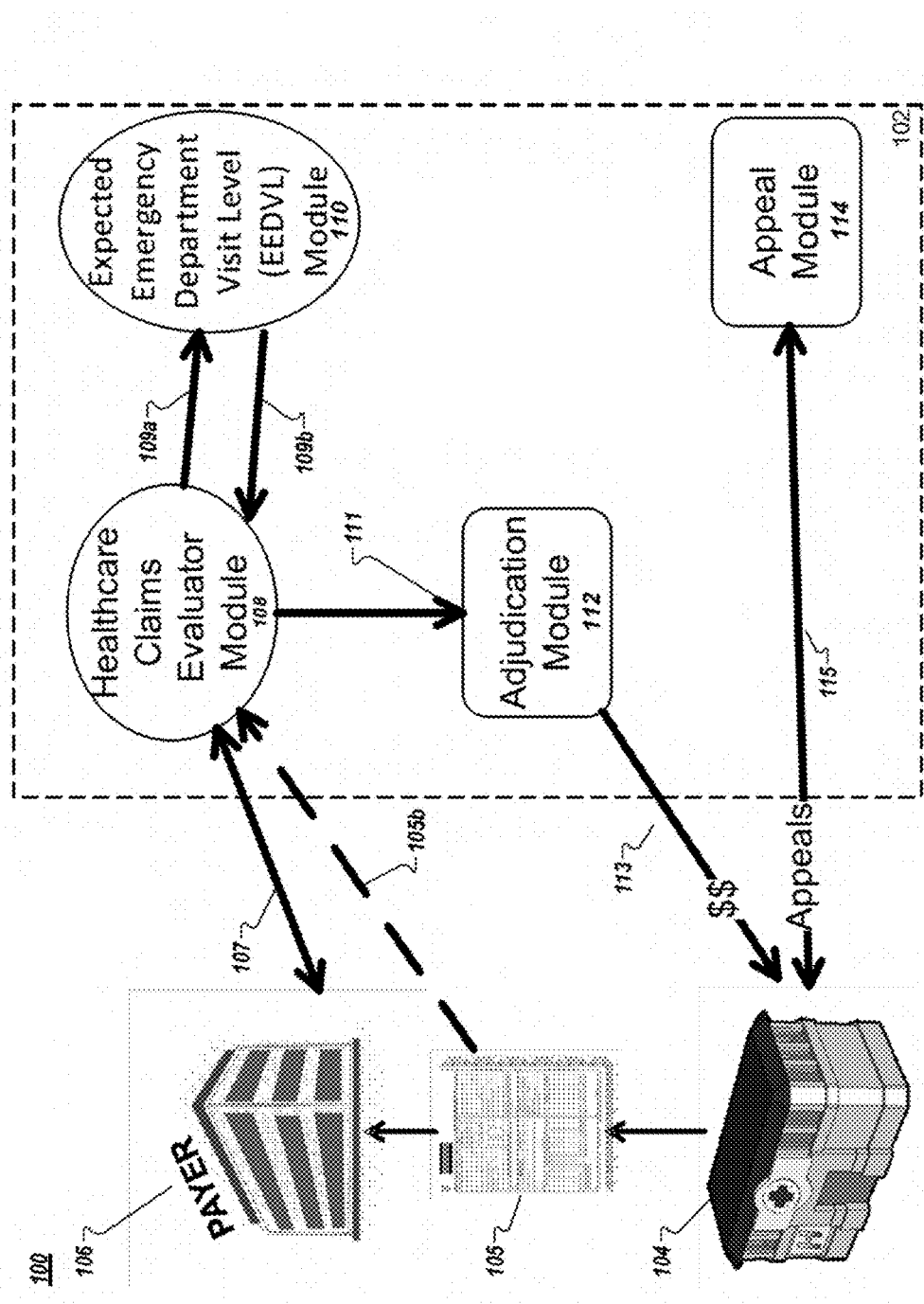
Figure 2:
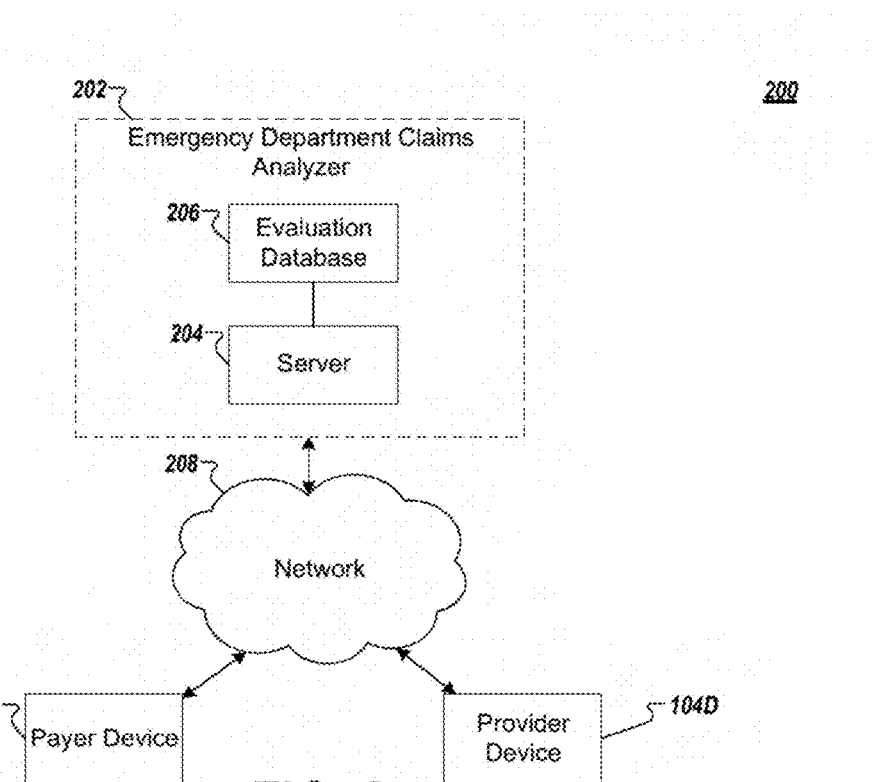
Figure 3:
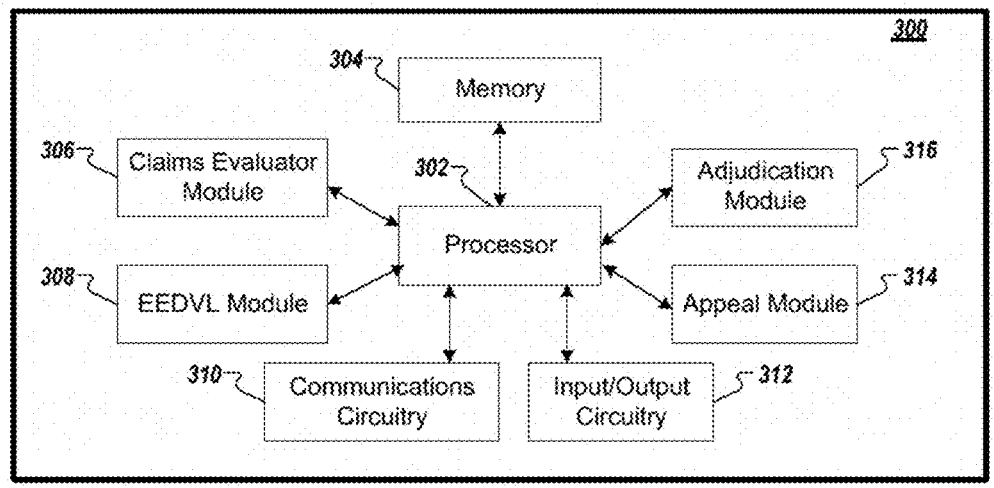

Having thus described certain example embodiments of the present disclosure in general terms, reference will now be made to the accompanying drawings, which are not necessarily drawn to scale, and wherein:

FIG. 1 shows an example system process diagram, in accordance with an example embodiment of the present invention;

FIG. 2 shows an example system diagram, in accordance with an example embodiment of the present invention;

FIG. 3 illustrates a schematic block diagram of circuitry used in association with a healthcare claims evaluator computing device, in accordance with some example embodiments;

FIGS. 4A-B illustrate example lookup tables in a standard value database in accordance with some example embodiments;

FIG. 5 illustrates an example lookup table in an extended value database in accordance with some example embodiments;

FIG. 6 illustrates an example lookup table in a patient complexity adjustment database in accordance with some example embodiments; and FIGS. 7-12 illustrate detailed flowcharts describing example operations for deriving an expected emergency department visit level (EEDVL).

DETAILED DESCRIPTION

Various embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

As used herein, the terms "data," "content," "information," and similar terms may be used interchangeably to refer to data capable of being transmitted, received, and/or stored in accordance with embodiments of the present invention. Thus, use of any such terms should not be taken to limit the spirit and scope of embodiments of the present invention. Further, where a computing device is described herein to receive data from another computing device, it will be appreciated that the data may be received directly from the another computing device or may be received indirectly via one or more intermediary computing devices, such as, for example, one or more servers, relays, routers, network access points, base stations, hosts, and/or the like, sometimes referred to herein as a "network." Similarly, where a computing device is described herein to send data to another computing device, it will be appreciated that the data may be sent directly to the another computing device or may be sent indirectly via one or more intermediary computing devices, such as, for example, one or more servers, relays, routers, network access points, base stations, hosts, and/or the like.

As used herein, the term "treatment code" refers to any medical code set utilized to communicate uniform or standardized information about medical services and procedures provided to a patient. Treatment codes may utilize International Statistical Classification of Diseases and Related Health Problems Tenth Revision, Clinical Modification (ICD-10-CM), Current Procedural Terminology (CPT), Healthcare Common Procedure Coding System (HCPCS), or other similar standardized coding conventions. The treatment code(s) may be received in a system in the form of a standard data set such as an EDI 8371 (or CMS Form 1450/UB-04).

As used here, the term "expected emergency department visit level (EEDVL)" refers to a derived level between 1 and 5 which corresponds to respective CPT visit codes 99281 through 99285 and/or HCPCS visit codes G0380 through G0384.

Example System Process

FIG. 1 shows an example system process diagram 100 for deriving an expected emergency department visit level (EEDVL). An emergency department healthcare provider 104 may include any type of healthcare provider or healthcare provider institution which provides emergency medicine or emergency department acute care services. For example, provider 104 may include a hospital, urgent care center, or independent emergency department clinic. Generally, when a patient visits or is admitted into an Emergency Department, such as provider 104, the primary reason is to diagnose an acute or emergency condition. The treatment provided is generally referred to by healthcare providers as evaluation and management (E/M). The E/M is then coded or classified for payment by the provider 104 using a set of standardized treatment codes such as Emergency Current Procedural Terminology (CPT) (e.g. visit level codes) developed, maintained, and copyrighted by the American Medical Association (AMA) or Healthcare Common Procedure Coding System (HCPCS) codes developed, maintained, and copyrighted by CMS. The Emergency CPT codes represent the effort, work, and cost incurred by the provider 104 in treating the patient and determining a final diagnosis. These codes are not meant to specifically capture the cost of any additional discreet procedures, such as lab tests etc., which will be separately billed, but merely the effort and resource usage that cannot be captured by other claims or codes. As described above, each different emergency health provider or facility may implement their own guidelines for E/M treatment coding, although these guidelines must reasonably relate the intensity of emergency department/facility resources to the levels of effort represented by the codes. The guidelines must generally utilize the eleven criteria for facility billing guidelines maintained by the CMS Hospital Outpatient Prospective Payment System (OPPS). However, given that these facility billing guidelines are broad in nature, they still allow flexibility in the coding schemes and thus allow for increasing overcoding of E/M treatment codes. Furthermore, since there is no national standard that governs E/M coding, it is often the case that various providers 104 utilize inconsistent E/M coding practices.

As shown in FIG. 1, healthcare provider 104 is responsible for filing a claim set 105 with a payer 106, who in turn will pay for some or all of the emergency treatment provided to a patient. In some example embodiments, the payer 106 may include an insurance company, self-insured employers, or other institutional payer such as CMS. The claims 105 may be in the form of an industry standard Uniform Bill (UB) 04, also known as CMS-1450 or the electronic equivalent of the UB-04 (an EDI 8371.). In some examples, the claims 105 may include claims for non-emergency treatment provided to a patient. For example, if a patient is admitted for an inpatient stay from an emergency department the claims 105 will reflect both the emergency treatment and treatment provided during the inpatient stay. While the process described herein is directed to deriving an expected emergency-department visit level, the process may also be applied to other level based medical code claims set, such as other types of facility based E/M code sets.

As shown in FIG. 1, the payer may then submit claims input/output 107 to a healthcare claims evaluator platform 102 for evaluation and verification of the claims coded levels which were determined by the provider 104. While illustrated in FIG. 1 as a separate entity from the payer 106, in some cases the platform 102 may be hosted by computing equipment maintained by the payer 106. The input/output 107 may be a set of healthcare claims for one patient's visit to an emergency department, such as claim set 105, or may be a batch or collection of healthcare claim sets, including several different claim sets 105. The healthcare claims evaluator platform 102 includes several modules to aid in the evaluation of the claims data and the settlement of any disputes or conflicts between the classification or coding of the claims by the platform 102 and the provider 104. In some examples, the provider 104 may submit the claim set 105 directly to the healthcare claims evaluator platform directly, such as shown by claim set 105b. This allows the payer to receive a preprocessing or assessment of the claims 105 prior to submitting the claims 105 to the payer 106. The healthcare claims evaluator module 108 may be configured to receive input/output 107 and determine what functions or other modules of the platform 102 should be performed or invoked. Input/output 107 may also include outputs from the healthcare claims evaluator platform 102, such as the outputs from the modules of the platform. For example, as most directly related to the operations described herein, the healthcare claims evaluator module 108 may determine that a given claim set 105 includes emergency department visit level or E/M treatment codes that require evaluation and verification by an expected emergency department visit level (EEDVL) module 110. The healthcare claims evaluator module 108 may also be configured to parse the healthcare claims for healthcare codes and exclude non-E/M codes from further processing or from processing by the EEDVL module 110.

The EEDVL module 110 may receive a full claim set such as claim set 105 as an input 109a from the module 108. Alternatively, the input 109a may include a collection of different claim sets 105 or even subsets of a single claim set 105 (e.g., individual claims codes parsed from a claim set 105 by healthcare claims evaluator module 108). The EEDVL module 110 may also exclude claim codes from further processing or in the derivation of the EEDVL based on criteria such as the patient condition or age. The EEDVL module then derives the EEDVL from the treatment codes by deriving several discrete components including a standard value, an extended value, and a patient complexity adjustment, and combining these components to derive the EEDVL from a threshold table. The output 109b of the EEDVL module 110 will comprise the expected visit level or EEDVL of the claims derived based on the operations, as further described in relation to FIGS. 2-12.

The adjudication module 112 and the appeal module 114 are configured to handle the output 111 from the modules 108 and 110 and provide a report to the payer 106 and/or provider 104. For example, if the expected visit level is different from the visit level claimed by the provider 104, the adjudication module 112 may report an output 113, which may include the EEDVL, along with a notification that a payout for the claimed emergency department visit level is different from the emergency department visit level coded by the provider. The adjudication module 112 may also determine an appropriate payout for the claim set 105 and transmit the payment to the provider 104.

The adjudication module 112 may also adjust or apply further logic to the EEDVL based on configurations from the payer 106 (or the provider 104 if the provider submits claim set 105b). For example, the adjudication module 112 may be configured to not alter the amount paid out to the provider 104 based on the EEDVL. The adjudication module 112 may be also configured to change the derived EEDVL based on information received in claim set 105, such as limiting the difference between the EEDVL and a claimed emergency department visit level.

The appeal module 114 may receive an appeal or request for explanation from the provider 104. The appeal module then produces a detailed report of how the expected visit level was derived, including the factors for deriving the discrete components of the EEDVL. The appeals module may also be configurable based on the preferences of payer 106.

As one example of this process, a patient may visit an emergency department of a hospital (provider 104) for a minor injury, such as a bee sting. If the bee sting is relatively minor and the patient is only having a mild allergic reaction, the E/M treatment code claimed by the provider 104 may only be a level 1 or a level 2. The provider 104 may submit a claim set 105 coded at a level 3 (a mid-range cost) to the payer 106, which then submits the claim set 105 to the platform 102. Although treating a minor bee sting should objectively be coded at a lower cost level, the overcoding to a level 3 may not be a result of malicious intent to overcharge on the part of the provider, but simply a quirk in the procedure used by provider 104 to implement the loose guidelines for classifying E/M codes set forth by CMS OPPS. However, while traditional systems would pay the claim at a level 3, example embodiments described herein may not. Instead, the EEDVL module may then derive, from the treatment codes in the claim set 105, that the EEDVL is a level 1. The adjudication module may then output (output 113) to the provider 104 that the EEDVL is a level 2 and provide payment to the provider based on this lower cost level. If the provider 104 disagrees with the EEDVL provided by the adjudication module 112, the provider can begin an appeals process 115 which is handled by the appeal module 114. For example, if the provider believes that the EEDVL is incorrect and would like to appeal the decision, the provider 104 may transmit an appeal to platform 102, which may reexamine the derived EEDVL or adjudication decisions made by modules 110 or 112.

The processes and functions of the system process diagram are described in more detail in relation to FIGS. 2-12.

Example System Architecture

Methods, apparatuses, and computer program products of the present invention may be embodied by any of a variety of devices. For example, the method, apparatus, and computer program product of an example embodiment may be embodied by a networked device, such as a server or other network entity, configured to communicate with one or more devices, such as one or more client devices. Additionally or alternatively, the computing device may include fixed computing devices, such as a personal computer or a computer workstation. Still further, example embodiments may be embodied by any of a variety of mobile terminals, such as a portable digital assistant (PDA), mobile telephone, smartphone, laptop computer, tablet computer, or any combination of the aforementioned devices.

FIG. 2 discloses an example computing system within which embodiments of the present invention may operate. For example, the healthcare claims evaluator platform 102 may be embodied on the Emergency Department Claim Analyzer (EDC Analyzer) computing system 202. While platform 102 is described herein as embodied on the EDC analyzer computing system 202, the computing system 202 may process health claims that are not emergency department specific. Healthcare claims payers 106 as described above may submit healthcare records, for example healthcare claims, to a EDC Analyzer computing system 202 via a network 208 (e.g., the Internet, or the like) using a payer computing device (payer device 106D). The emergency department healthcare provider may also submit healthcare records, for example healthcare claims, to the payer 106 through network 208 using an emergency department healthcare computing device (provider device 104D). As described herein, the EDC Analyzer computing system 202 may also be in communication with the emergency department healthcare provider 104 through network 208 and device 104D.

The computing devices 106D and 104D, may be embodied by any computing devices known in the art. For example, these devices may include desktop computers, laptop computers, smartphones, netbooks, tablet computers, wearable devices, and/or any combination of devices or entities adapted to perform the functions, operations, and/or processes described herein, and the electronic data may be provided using various transmission modes and/or protocols associated with these devices.

Additionally or alternatively, the payers and emergency department healthcare providers, and other third parties may interact with the EDC Analyzer computing system 202 via a web browser. As yet another example, the devices 106D and 104D may include various hardware or firmware designed to interface with the EDC Analyzer computing system 202 (e.g., where an example device 106D or 104D is a purpose-built device offered for the primary purpose of communicating with the EDC Analyzer computing system 202).

The EDC Analyzer computing system 202 may comprise a server 204 in communication with an evaluation database 206. The server 204 may be embodied as a computer or computers as known in the art. The server 204 may receive electronic data such as a set of healthcare claims (e.g., claim sets 105) from various sources, including but not necessarily limited to the devices 106D and 104D, and may be operable to receive and process healthcare claims and corresponding treatment codes provided by these devices.

The evaluation database 206 may be embodied as a data storage device such as a Network Attached Storage (NAS) device or devices, or as a separate database server or servers. The evaluation database 206 also stores information accessible by the server 204 to facilitate the operations of the EDC Analyzer computing system 202. For example, the evaluation database 206 may include, without limitation: user account credentials for system administrators, healthcare payers, healthcare providers, and other third parties; and sets of structured data (e.g., relational databases or lookup tables) correlating healthcare claims and treatment codes with determined standard values, extended values, patient complexity adjustments, or expected visit levels for emergency department visit levels known and/or determined via processing of the healthcare claims by the EDC Analyzer computing system 202, and/or the like. As may be most relevant to embodiments described herein, evaluation database 206 may also include claim level classification tables that contain information regarding the classification of healthcare claims or any other methodology that identifies and evaluates the healthcare claims and treatment codes within a database of healthcare information.

Example Apparatus for Implementing Embodiments of the Present Invention

The server 204 may be embodied by one or more computing devices, such as apparatus 300 shown in FIG. 3. As illustrated in FIG. 3, the apparatus 300 may include a processor 302, a memory 304, input/output circuitry 312, communications circuitry 310, and circuitry to implement various modules such as claims evaluator module 306, EEDVL module 308, adjudication module 316, and appeal module 314. The apparatus 300 may be configured to execute the operations described above with respect to FIGS. 1-2 and below with respect to FIGS. 7-12. Although these components 302-316 are described in part using functional limitations, it should be understood that any implementations necessarily include the use of particular hardware. It should also be understood that certain of these components 302-316 may include similar or common hardware. For example, multiple modules or circuitries may leverage use of the same processor, network interface, storage medium, or the like, to perform their associated functions, such that duplicate hardware is not required for each distinct module or circuitry. The terms "circuitry" and "module" as used herein therefore includes particular hardware configured to perform the respective functions described herein.

Of course, while the term "circuitry" or "module" should be understood broadly to include hardware, in some embodiments it may also include software for configuring the hardware. In some embodiments, "circuitry" or "module" may include processing circuitry, storage media, network interfaces, input/output devices, and the like. In some embodiments, other elements of the apparatus 300 may provide or supplement the functionality of particular circuitries or modules. For example, the processor 302 may provide processing functionality, the memory 304 may provide storage functionality, the communications circuitry 310 may provide network interface functionality, and the like.

The processor 302 (and/or co-processor or any other processing circuitry assisting or otherwise associated with the processor) may be in communication with the memory 304 via a bus for passing information among components of the apparatus. The memory 304 may be non-transitory and may include, for example, one or more volatile and/or non-volatile memories. In other words, the memory may be an electronic storage device (e.g., a computer readable storage medium). The memory 304 may be configured to store information, data, content, applications, instructions, or the like, for enabling the apparatus to carry out various functions in accordance with example embodiments of the present invention.

The processor 302 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 302 may be configured to execute instructions stored in the memory 304 or otherwise accessible to the processor. Alternatively or additionally, the processor may be configured to execute hard-coded functionality. As such, whether configured by hardware or software methods, or by a combination of hardware with software, the processor may represent an entity (e.g., physically embodied in circuitry) capable of performing operations according to an embodiment of the present invention while configured accordingly. Alternatively, as another example, when the processor is embodied as an executor of software instructions, the instructions may specifically configure the processor to perform the algorithms and/or operations described herein when the instructions are executed.

In some embodiments, the apparatus 300 may include input/output circuitry 312 that may, in turn, be in communication with processor 302 to provide output to a user and, in some embodiments, to receive an indication of user input. The input/output circuitry 312 may comprise a user interface and may include a display and may comprise a web user interface, a mobile application, a client device, or the like. In some embodiments, the input/output circuitry 312 may also include a keyboard, a mouse, a touch screen, touch areas, soft keys, or other input/output mechanisms. The processor and/or user interface circuitry comprising the processor may be configured to control one or more functions of one or more user interface elements through computer program instructions (e.g., software and/or firmware) stored on a memory accessible to the processor (e.g., memory 304, and/or the like).

The communications circuitry 310 may be any means such as a device or circuitry embodied in either hardware or a combination of hardware and software that is configured to receive and/or transmit data from/to a network and/or any other device, circuitry, or module in communication with the apparatus. In this regard, the communications circuitry 310 may include, for example, a network interface for enabling communications with a wired or wireless communication network. For example, the communications circuitry 310 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s).

The claims evaluator module 306, the EEDVL module 308, the adjudication module 316, and the appeal module 314 may be any means such as a device or circuitry embodied in either hardware or a combination of hardware and software that is configured to perform the corresponding functions of these components that are described herein. It should be appreciated that, in some embodiments, the claims evaluator module 306, the EEDVL module 308, the adjudication module 316, and/or the appeal module 314 may include a separate processor, specially configured field programmable gate array (FPGA), or application specific interface circuit (ASIC) to perform the corresponding functions described herein. Accordingly, in one fashion or another, the claims evaluator module 306, the EEDVL module 308, the adjudication module 316, and the appeal module 314 are therefore implemented using hardware components of the apparatus which may in turn be configured by either hardware or software.

As will be appreciated, any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

In some embodiments, one or more external systems (such as a remote cloud computing and/or data storage system) may also be leveraged to provide at least some of the functionality discussed herein.

As described above and as will be appreciated based on this disclosure, embodiments of the present invention may be configured as methods, mobile devices, backend network devices, and the like. Accordingly, embodiments may comprise various means including entirely of hardware or any combination of software and hardware. Furthermore, embodiments may take the form of a computer program product stored on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Example Operations Performed by the EDC Analyzer Computing Device

Having described the circuitry comprising some embodiments of the present invention, it should be understood that the EDC Analyzer computing system 202 may advantageously derive an expected emergency department visit level (EEDVL) in a number of ways. In accordance with example embodiments, FIGS. 4A-6 illustrate exemplary lookup tables that may store the various values used to derive an EEDVL, while FIGS. 7-12 illustrate flowcharts containing specific operations performed to efficiently derive the EEDVL utilizing lookup tables such as those illustrated in FIGS. 4A-6.

Turning now to FIGS. 4A and 6, a series of example lookup tables are illustrated in accordance with some example embodiments. The lookup tables may comprise various databases that in turn may be stored in the evaluation database 206, memory 304, or any other storage means accessible to the EDC Analyzer computing system 202. It should be understood that while these lookup tables are illustrated using one specific layout, other example embodiments may use different logical structures, and that these differences may be arbitrary, be based on the type of claim codes presented, or based on the requirements of the derivation methodologies that may be used in the various embodiments contemplated herein. Accordingly, while the lookup tables in FIGS. 4A-6 are illustrated as a chart or table for exemplary or visual exposition purposes, the values shown may also be presented in other visual forms such as graphs, lists, and other data forms such as a relational database or relational data structure. For example, the output from the appeal module 314 may include a visual representation of the lookup tables including the claim/code data and the data used in the derivation of the EEDVL in any of the visual forms described above. Accordingly, it is just for ease of description that the relational data shown in FIGS. 4A-6 are discussed herein as a series of lookup tables.

In general, the various values used in deriving the EEDVL and stored in the lookup tables illustrated in FIGS. 4A-6 are generated based on historical data including past treatment codes, facility cost data as well as expert opinion regarding the scores or levels that various treatment codes require in the derivation of the EEDVL. For example, a standard value comprises a standard resource valuation for each presenting problem. These valuations (or weights) include nursing and ancillary staff time (for a routine arrival, triage, registration, basic patient/family communications, and a routine discharge), the room, creation of a medical record, coding, and billing. Extended values account for the emergency department facility resources (including staff time) expended so that orders are noted, communicated, and followed up as needed. These values do not include time spent in the actual performance of separately billable tests/procedures. The patient complexity adjustment measures the incremental facility cost associated with complicating conditions. The conditions typically align with greater than usual use of facility resources and time. These patient complexity adjustments (or weights) are based on analyses of the additional services provided to patients with these complicating factors. This analysis resulted in the assignment of weights in proportion to facility resource time and effort.

FIG. 4A illustrates a first lookup table for use in deriving a standard value using a set of treatment codes. In some examples, the treatment codes may comprise reason for visit (RFV) diagnosis codes extracted from claim sets 105 submitted to the platform 102. The columns of the lookup table in FIG. 4A represent information relating to the treatment codes, which are shown in each row. Columns A and B represent internal identification numbers for the reason for visit (RFV) diagnosis codes. Column C contains a PSCA (patient complexity adjustment) score (these values may roughly correlate to E/M levels). Columns D and E detail, in plain language, the "Major" and "Minor" medical problems. Column F details the problem sector or area of the patient's body that is experiencing the medical problem. Finally, column G includes the one or more diagnosis codes, which are the standard codes for a presenting problem. In this regard, diagnosis codes are represented by ICD-10-CM codes, as shown in column G in the lookup table 4A. For example, the ICD-10-CM codes S62.92 and S63.005 as shown in the field at row 8 and column G represent an injury to an extremity (row 8, column D) and specifically the left wrist (row 8, column F). The PSCA score is represented in row 8, column C and is a "4" which correlates to a higher set of base or standard costs provided by the emergency department in contrast to treatment such as "wound drain evaluation" as shown in row 16 which is a PSCA score of 2 (row 16, column C). This PSCA score will then be converted into a standard value by using a conversion table such as that shown in Table 1 below.

TABLE 1

| PSCA to Standard Value ||
| PCSA | Standard Value |
| --- | --- |
| 1 | 100 |
| 2 | 300 |
| 3 | 400 |
| 4 | 600 |
| 5 | 1000 |

For example, the PSCA score 4 corresponds to a standard value (weight) of 600, which will thereafter be used in the derivation of the EEDVL.

FIG. 4B also illustrates a lookup table, but this lookup table is designed for use in deriving a standard value using a set of treatment codes and accounting for additional acuity factors such as age and gender. Column A represents a numbering identification, and column D represents the identification of the treatment code (as labelled in column B of the lookup table in FIG. 4A). Columns B, C, and G identify the problem name, problem sector, and notes about the problem in plain language, respectively. Column F represents acuity factors such as sex and age, which apply to the various problems identified in each row. In some examples, similar conditions may have different levels of care required by the emergency department depending on the sex or age of the patient. Thus, patient acuity is an important factor in deriving an expected emergency department visit level. For example, as shown in rows 5 and 6 of the lookup table in FIG. 4B, treating apnea in children less than 24 months old requires more emergency department resources and thus has a higher PSCA score (5 as seen in row 5 column E) than a PSCA score treating apnea for adults aged twelve and older (which has a PSCA score of 4, as seen in row 6 column E).

FIG. 5 illustrates a lookup table for use in deriving an extended value using a set of treatment codes and specifically for identifying one or more resource utilization codes from an extended value database. The extended value is not meant to account for the cost of facility testing and workups (i.e., lab orders), but is used to aid in the determination of the level of care provided by the emergency department. Each of the columns of lookup table 5 represents information relating to treatment codes. Column A shows the category of the resource utilization. Column B identifies the treatment code (e.g., CPT code). Columns C and D provide plain language information about the procedures conducted by the emergency department for each treatment code. In some examples, the resource utilization codes may be correlated to a weight or extended value score shown in Table 2, such that each of the resource utilization codes has a determined weight for use in an extended value. For example, involvement of a lab order, as shown in row 1 of the lookup table shown in FIG. 5, corresponds to an extended value score of 100. In an example where lab orders are the only resource utilization codes present, the extended value would be 100 (regardless of the number of lab orders actually made).

TABLE 2

Extended Value Scores

| Type | Weight |
| --- | --- |
| Lab Orders | 100 |
| X-ray - plain film Orders | 100 |
| EKG/RT/Ancillary Service/Other Diagnostic Orders | 100 |
| CT/MRI/Ultrasound Orders | 200 |

In some examples, the extended value is additive or combines the extended value scores. For example, if both a lab order as shown in row 1 and an X-ray as shown in row 14 are present in the treatment codes, the extended value scores would be 100 for the lab orders and 100 for the X-rays. The resulting extended value would be the sum of the scores, which is 200. But if just the X-rays were ordered (and no lab orders were made), then the facility intensity value would be 100 (regardless of how many X-rays were ordered).

FIG. 6 illustrates another lookup table, this one for use in deriving a patient complexity adjustment using a set of treatment codes specifically for identifying values from a patient complexity database. A patient complexity adjustment is designed to capture complicating factors that may not be represented by the reason for visit diagnosis codes, and may be derived from underlying patient conditions complicated by the reason for visit. Column A includes the treatment code such as the ICD-10-CM Code. Column D shows in plain language the title/description of the treatment code. Column B shows the patient complexity adjustment assigned to the treatment code. In some embodiments, a claim set 105 may only comprise one treatment code, which will have a corresponding complexity score. In such embodiments, the patient complexity adjustment will be that value. In other embodiments, there may be two or more treatment codes with complexity scores present in a healthcare claim set. In these embodiments, the patient complexity adjustment will be equal to the highest of the two or more scores.

Figure 7:
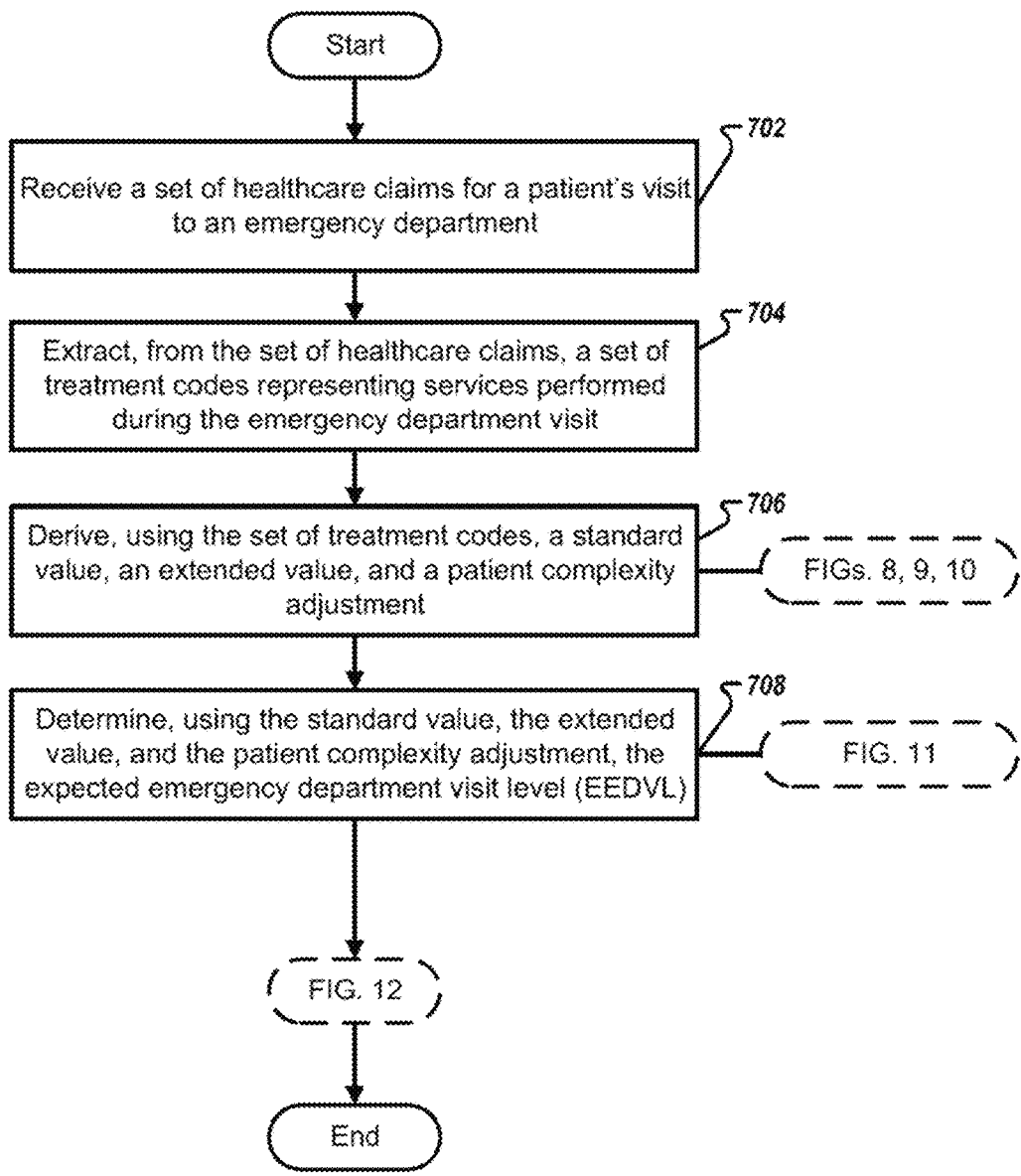

Turning now to FIG. 7, a flowchart is provided that illustrates a detailed sequence of example operations for deriving an expected emergency department visit level (EEDVL), in accordance with some example embodiments. As noted previously, these operations may be performed by the EDC Analyzer computing system 202, with the assistance of, and/or under the control of a computing device such as apparatus 300.

In operation 702, apparatus 300 includes means, such as communications circuitry 310, input/output circuitry 312, or the like, for receiving a set of healthcare claims for a patient's visit to an emergency department. For example, communications circuitry 310 may receive the set of healthcare claims from a payer device 106D through a network 208. Furthermore, the set of healthcare claims may be received from a variety of sources, such as from payers 106, e.g. insurers, and/or providers 104 using one or more devices 106D or 104D, or the like. The healthcare claims also need not be received in a single transaction, but can be received periodically or on an ad hoc basis and stored in an evaluation database 206 for later use. The set healthcare claims may comprise one or more sets of claim codes representing one or more patient visits to one or more emergency departments. For example, the set of healthcare claims may include two different patient visits for two patients at different emergency department facilities.

In operation 704, apparatus 300 includes means, such as claims evaluator module 306 or the like, for extracting, from the set of healthcare claims (e.g., claim set 105), a set of treatment codes representing services performed during the emergency department visit (e.g. the patient visit to the emergency department) and the condition of the patient. For example, the set of healthcare claims, when received, may be in raw data form or in the EDI 8371 form as described above, and the apparatus 300 may thus include means, such as claims evaluator module 306 or the like, for parsing the set of healthcare claims into a set of treatment codes.

In an instance in which the set of healthcare claims includes healthcare claims or treatment codes unrelated to a patient's visit to an emergency department and/or does not include healthcare claims or treatment codes related to an emergency department visit, the healthcare claims or treatment codes that are unrelated to a patient's emergency department visit will be further processed and evaluated by claims evaluator module 306.

In operation 706, apparatus 300 includes means, such as EEDVL module 308 or the like, for deriving, using the set of treatment codes, a standard value, an extended value, and a patient complexity adjustment. For example, the set of treatment codes may be correlated to stored scores and values to derive each of the standard value, extended value, and patient complexity adjustment. These operations are described in further detail in relation to FIGS. 8, 9, and 10.

In operation 708, apparatus 300 includes means, such as EEDVL module 308 or the like, for determining an EEDVL, using the standard value, the extended value, and the patient complexity adjustment. In some examples, the standard value, the extended value, and the patient complexity adjustment may be combined into a final score and compared with various thresholds to determine the corresponding EEDVL. This operation is further described in relation to FIG. 11.

As shown in FIG. 7, the apparatus 300 may also include further means including any of the modules/circuitry to optionally further handle the EEDVL after it has been derived. Some examples of this further processing are further described below in relation to FIG. 12.

Figure 8:
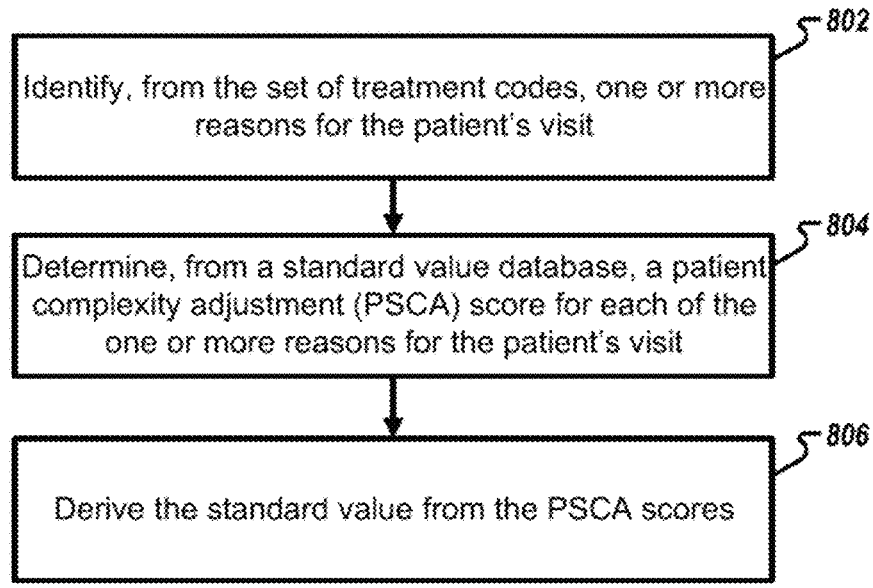

Turning now to FIG. 8, a flowchart is provided that illustrates a detailed sequence of example operations for deriving the standard value, in accordance with some example embodiments. As noted previously, these operations may be performed by an EDC Analyzer computing system 202, with the assistance of, and/or under the control of a computing device such as apparatus 300.

In operation 802, apparatus 300 includes means, such as EEDVL module 308 or the like, for identifying, from the set of treatment codes, one or more reasons for the patient's visit. In some examples, EEDVL module 308 may determine from a set of treatment codes that a patient received E/M treatment from provider 104 for an injury to their right wrist which corresponds to a treatment code such as ICD-10-CM S69.81XA. In one example, one or more reasons for the patient's visit may comprise RFV ICD-10-CM codes which are submitted on the 8371 in a distinct field separate from other ICD-10 codes (other codes include the principal diagnosis and secondary or symptom diagnoses. In the case where the treatment codes contain multiple RFV codes and thus multiple PSCA score matches, the highest PSCA score value is the standard value used.) In an instance, the treatment codes include RFV ICD-10 codes that do not contain a match on the standard value table, then that set treatment codes are processed as received by the provider and an EEDVL is not derived.

In operation 804, apparatus 300 includes means, such as EEDVL module 308 or the like, for determining, from a standard value database, a PSCA score for each of the one or more reasons for the patient's visit. For example, the EEDVL module 308 may utilize the lookup table in FIG. 4A (which may be stored in the standard value database) for this purpose. In the example of an injury to a patient's right wrist, the EEDVL module 308 may determine that the PSCA score is a 3, as shown in row 6, column C of the lookup table shown in FIG. 4A.

In operation 806, apparatus 300 includes means, such as EEDVL module 308 or the like, for deriving the standard value from the PSCA score scores. For example, the EEDVL module 308 may take the PSCA score of 3 for the patient's injured wrist and determine the standard value of 400 from Table 1. This standard value may then be stored in memory 304 or evaluation database 206 for further use by the apparatus 300.

Figure 9:
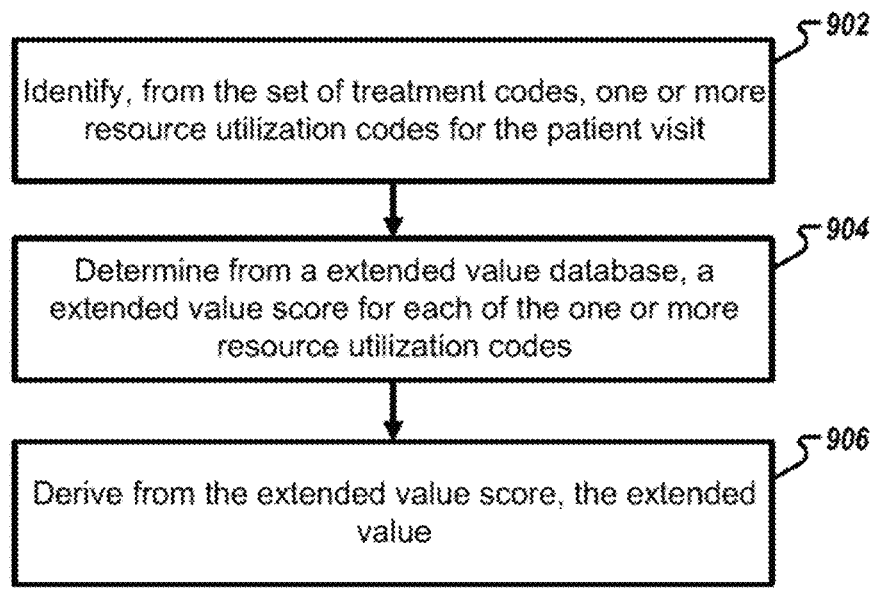

Turning now to FIG. 9, the provided flowchart illustrates a detailed sequence of example operations for deriving the extended value, in accordance with some example embodiments. As noted previously, these operations may be performed by the EDC Analyzer computing system 202, with the assistance of, and/or under the control of a computing device such as apparatus 300.

In operation 902, apparatus 300 includes means, such as EEDVL module 308 or the like, for identifying, from the set of treatment codes, one or more resource utilization codes for the patient's visit. In some examples, the EEDVL module 308 may determine, from a set of treatment codes, that specific resources were used in the treatment of the patient, such as the patient receiving a specific test from provider 104 for the injury to their right wrist which corresponds to a treatment code such as 73110.

In operation 904, apparatus 300 includes means, such as EEDVL module 308 or the like, for determining, from an extended value database, an extended value score for each of the one or more resource utilization codes. For example, the EEDVL module 308 may utilize a lookup table such as that shown in FIG. 5 stored in the extended value database to determine that that test conducted was an X-ray on the wrist. If the X-ray is the only resource utilization code present, the EEDVL module 308 may then correlate the X-ray to the extended value score as shown in table 2 of 100. If there are further resource utilization codes, such as for lab orders, EKGs, MRIs, or other utilized facility resource, the EEDVL module 308 will also determine extended value scores for each of the present categories.

In operation 906, apparatus 300 includes means, such as EEDVL module 308 or the like, for deriving, from the extended cost scores, the extended value. In some examples, the EEDVL module 308 may sum each of the extended value scores into the extended value. This extended value may then be stored in memory 304 or evaluation database 206 for further use by the apparatus 300.

Figure 10:
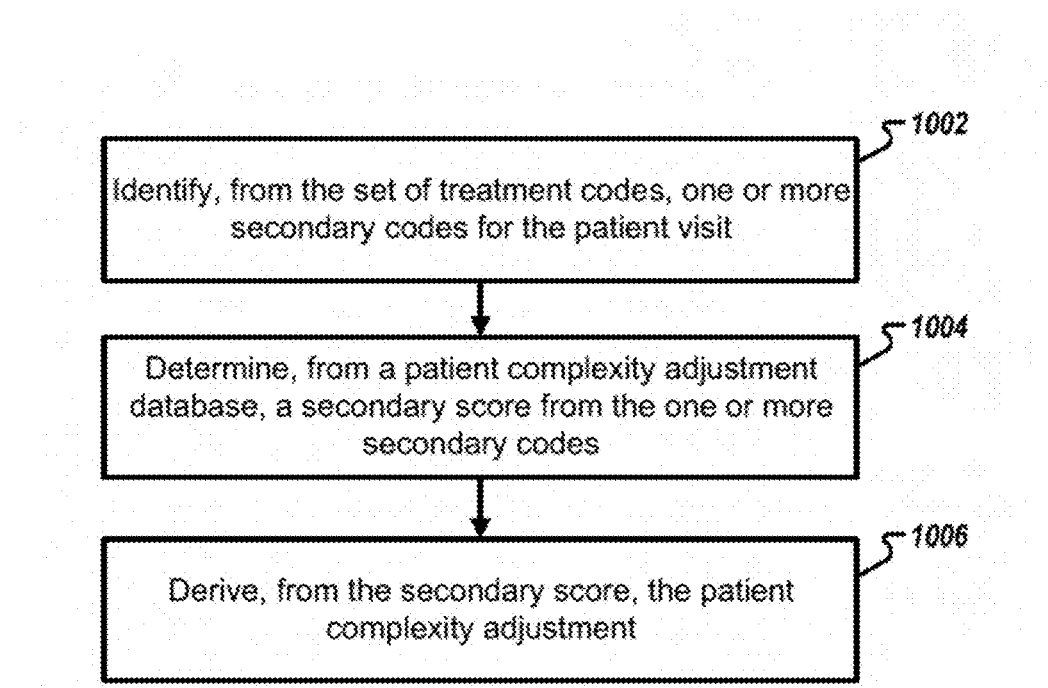

Turning now to FIG. 10, the provided flowchart illustrates a detailed sequence of example operations for deriving the patient complexity adjustment, in accordance with some example embodiments. As noted previously, these operations may be performed by the EDC Analyzer computing system 202, with the assistance of, and/or under the control of a computing device such as apparatus 300.

In operation 1002, apparatus 300 includes means, such as EEDVL module 308 or the like, for identifying, from the set of treatment codes, one or more secondary diagnosis codes for the patient visit (in some examples, the secondary diagnosis codes may also include the principal diagnosis code). These codes represent complicating factors that the emergency department has to take into consideration during the treatment of a patient. In some examples, the claim form CMS-1450/or electronic equivalent 8371 breaks the ICD-10 codes into specific category codes, there are RFV codes, primary/principal diagnosis and "other" supporting diagnoses—the RFV and primary have a specific labeled field in the claim. For example, the set of healthcare claims for the treatment of the wrist injury described above may include the ICD-10 codes G40.89 and R57.9 shown respectively in rows 13 and 33 of the lookup table in FIG. 6. The codes represent that the patient is experiencing seizures (row 13, column C) and is in shock (row 33, column C).

In operation 1004, apparatus 300 includes means, such as EEDVL module 308 or the like, for determining, from a patient complexity adjustment database, a complexity value from the one or more principal or secondary diagnosis codes. For example, the complexity scores for the ICD codes G40.89 and R57.9 are 189 (row 13, column B) and 27 (row 33, column B).

In operation 1006, apparatus 300 includes means, such as EEDVL module 308 or the like, for deriving, from the complexity scores the patient complexity adjustment. In some embodiments, the EEDVL module 308 derives the patient complexity adjustment as the highest of the complexity scores. For example, the value complexity score 189 is higher than the complexity score 27 resulting in a final patient complexity adjustment of 189.

Figure 11:
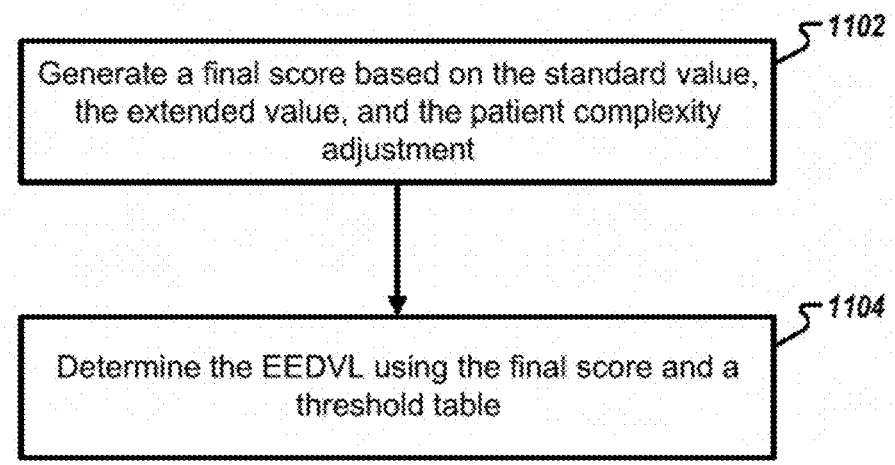

Turning now to FIG. 11 the provided flowchart illustrates a further detailed sequence of example operations for deriving the emergency department visit level. As noted previously, these operations may be performed by an EDC Analyzer computing system 202, with the assistance of, and/or under the control of a computing device such as apparatus 300.

In operation 1102, apparatus 300 includes means, such as EEDVL module 308 or the like, for generating a final score based on the standard value, the extended value, and the patient complexity adjustment. In some examples, generating the final score includes adding the standard value, the extended value, and the patient complexity adjustment into a final score. For example, for the healthcare claims relating to the wrist injury, the standard value 300, the extended value of 100, the patient complexity adjustment of 189 will combine for a final score of 589.

In operation 1104, apparatus 300 includes means, such as EEDVL module 308 or the like, for determining the EEDVL using the final score and a threshold table. In some examples, the threshold table comprises a set of thresholds ranges, such as a minimum value or points required to be in the threshold range, corresponding to a set of emergency department visit levels, wherein the final score is within a particular threshold range of the set of threshold ranges, and wherein the EEDVL comprises the emergency department visit level corresponding to the particular threshold range. In some examples, the threshold table may comprise Table 3 shown below.

TABLE 3

Final Score to EEDVL

| Visit Code | TVL | Score Range |
|---|---|---|
| 99281 | G0380 | Level 1 | 100-299 |
| 99282 | G0381 | Level 2 | 300-499 |
| 99283 | G0382 | Level 3 | 500-799 |
| 99284 | G0383 | Level 4 | 800-1299 |
| 99285 | G0384 | Level 5 | 1,300+ |

For example, for the healthcare claims relating to the wrist injury, the final score of 589 is above the minimum points or threshold for level 3, but below the minimum points or threshold for level 4 or within the score range 500-799. Thus the EEDVL will be a level 3 for the healthcare claim set. As shown in Table 3, the level 3 corresponds to the CPT visit code 99283 or G0382.

Figure 12:
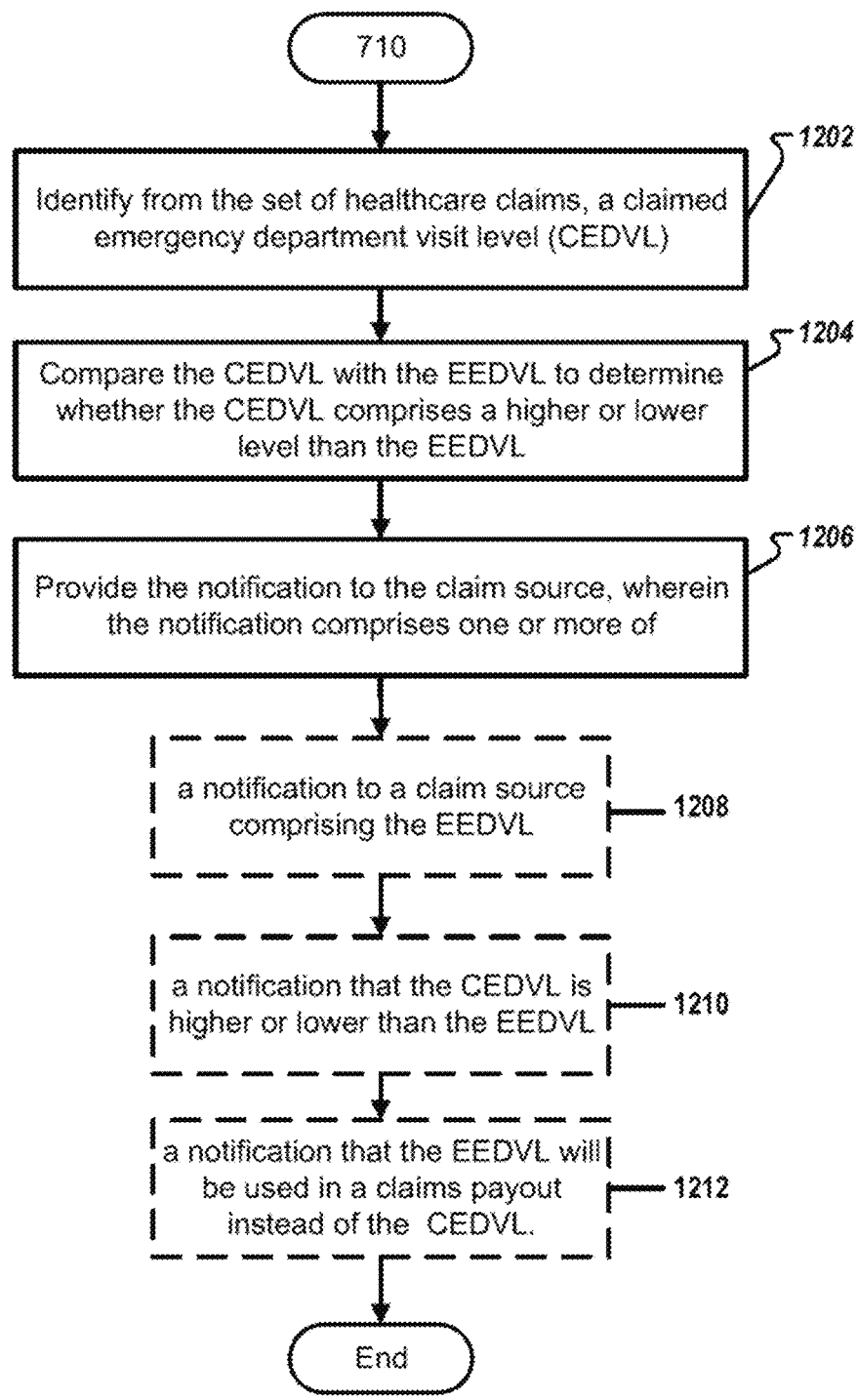

Turning now to FIG. 12, the provided flowchart illustrates additional optional operations for deriving an EEDVL, in accordance with some example embodiments. As noted previously, these operations may be performed by an EDC Analyzer computing system 202, with the assistance of, and/or under the control of a computing device such as apparatus 300.

In operation 1202, apparatus 300 includes means, such as adjudication module 316, or the like, for identifying, from the set of healthcare claims, a claimed emergency department visit level (CEDVL).

In operation 1204, apparatus 300 includes means, such as adjudication module 316, or the like, for comparing, the CEDVL with the EEDVL to determine whether the CEDVL comprises a higher or lower level than the EEDVL. In some examples, adjudication module 316, will apply further logic according to configurations set by the payer 106 to modify the EEDVL. For example, there may be limits on the number of visit level changes that will be considered between the EEDVL and the CEDVL. For example, the payer 106 could choose to only consider 2 visit level changes. In doing so, if the CEDVL is 2, the EEDVL can only be a 4 or 5. A change from a CEDVL of 2 to a EEDVL of 1 or 3 will not be considered. In another example, the adjudication module 316 may only change a monetary disbursement to a provider if the EEDVL is less than the CEDVL. Finally, the payer 106 could choose to only evaluate claim sets with a CEDVL of a specified value (1-5). For example, only claim sets with a CEDVL of 4 or 5 could be considered.

In operation 1206, apparatus 300 includes means, such as claims evaluator module 306, or the like, for providing the notification to a claim source, such as provider 104. In this regard, the notification may comprise one or more of a communication to a claim source comprising the EEDVL (box 1208), a notification that the CEDVL is higher or lower than the EEDVL (box 1210), or a notification the EEDVL will be used in a claims payout instead of the CEDVL (box 1212).

Many modifications and other embodiments of the inventions set forth herein will come to mind to one skilled in the art to which these inventions pertain having the benefit of the teachings presented in the foregoing descriptions and the associated specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A computer implemented method for deriving an expected emergency department visit level (EEDVL), the EEDVL comprising an expected medical claims coding level, the method comprising:

receiving, by one or more processors, a set of healthcare claims for a patient's visit to an emergency department, wherein the set of healthcare claims comprises a claimed emergency department visit level (CEDVL), the CEDLV comprising a claimed medical claims coding level;

extracting, by the one or more processors from the set of healthcare claims, a set of treatment codes indicative of (a) services performed during the patient's visit to the emergency department, and (b) one or more conditions associated with the patient's visit to the emergency department;

deriving, by the one or more processors, a standard value by:
automatically identifying, based at least in part on the set of treatment codes, data indicative of one or more reasons for the patient's visit to the emergency department,
automatically determining, based at least in part on the one or more reasons for the patient's visit to the emergency department and using a standard value lookup table, a patient complexity adjustment (PSCA) score, and
automatically deriving, based at least in part on the PSCA score, the standard value for the patient's visit to the emergency department, wherein the standard value comprises a standard resource valuation;

deriving, by the one or more processors and based at least in part on the set of treatment codes, an extended value indicative of resource utilization during the patient's visit to the emergency department;

deriving, by the one or more processors and based at least in part on the set of treatment codes, a patient complexity adjustment by:
automatically identifying, based at least in part on the set of treatment codes, one or more secondary codes for the patient's visit to the emergency department,
automatically determining, using a patient complexity adjustment lookup table, a secondary score based at least in part on the one or more secondary codes, and
automatically deriving, based at least in part on the secondary score, the patient complexity adjustment;

determining the EEDVL, by the one or more processors and based at least in part on the standard value, the extended value, and the patient complexity adjustment;

comparing, by the one or more processors, the CEDVL and the EEDVL to determine if the CEDVL and the EEDVL are different; and responsive to a determination that the CEDVL and the EEDVL are different, automatically (a) generating a notification comprising the CEDVL and the EEDVL, and (b) automatically transmitting the notification to a user account associated with the CEDVL.

2. The computer implemented method of claim 1, wherein deriving the extended value comprises:
   identifying one or more resource utilization codes for the patient visit;
   determining an extended value score for each of the one or more resource utilization codes; and
   deriving, from the extended value scores, the extended value.

3. The computer implemented method of claim 1, wherein deriving the extended value comprises summing the extended value scores for the one or more resource utilization codes.

4. The computer implemented method of claim 1, wherein deriving the EEDVL comprises:
   generating a final score based on the standard value, the extended value, and the patient complexity adjustment; and
   determining the EEDVL using the final score and a threshold table, wherein the threshold table comprises a set of threshold ranges corresponding to a set of emergency department visit levels, wherein the final score is within a particular threshold range of the set of threshold ranges, and wherein the EEDVL comprises the emergency department visit level corresponding to the particular threshold range.

5. A healthcare claim payer apparatus for deriving an expected emergency department visit level (EEDVL), the EEDVL comprising an expected medical claims coding level, the apparatus configured to:
   receive a set of healthcare claims for a patient's visit to an emergency department, wherein the set of healthcare claims comprises a claimed emergency department visit level (CEDVL) the CEDLV comprising a claimed medical claims coding level;
   extract, from the set of healthcare claims, a set of treatment codes indicative of (a) services performed during the patient's visit to the emergency department, and (b) one or more conditions associated with the patient's visit to the emergency department;
   derive a standard value by:
      automatically identifying, based at least in part on the set of treatment codes, data indicative of one or more reasons for the patient's visit to the emergency department,
      automatically determining, based at least in part on the one or more reasons for the patient's visit to the emergency department and using a standard value lookup table, a patient complexity adjustment (PSCA) score for each of the one or more reasons for the patient's visit, and
      automatically deriving, based at least in part on the PSCA score, the standard value for the patient's visit to the emergency department, wherein the standard value comprises a standard resource valuation;
   derive, based at least in part on the set of treatment codes, an extended value indicative of resource utilization during the patient's visit to the emergency department;
   derive, based at least in part on the set of treatment codes, a patient complexity adjustment by:
      automatically identifying, based at least in part on the set of treatment codes, one or more secondary codes for the patient's visit to the emergency department,
      automatically determining, using a patient complexity adjustment lookup table, a secondary score based at least in part on the one or more secondary codes, and
      automatically deriving, based at least in part on the secondary score, the patient complexity adjustment;
   determine the EEDVL, based at least in part on the standard value, the extended value, and the patient complexity adjustment;
   compare the CEDVL and the EEDVL to determine if the CEDVL and the EEDVL are different; and
   responsive to a determination that the CEDVL and the EEDVL are different, automatically (a) generate a notification comprising the CEDVL and the EEDVL, and (b) automatically transmit the notification to a user account associated with the CEDVL.

6. The apparatus of claim 5, wherein to derive the extended value the apparatus is further configured to:
   identify, from the set of treatment codes, one or more resource utilization codes for the patient visit;
   determine, by using an extended value lookup table, an extended value score for each of the one or more resource utilization codes; and
   derive, from the extended value scores, the extended value.

7. The apparatus of claim 6, wherein to derive the extended value the EEDVL module is further configured to sum the extended value scores for the one or more resource utilization codes.

8. The apparatus of claim 5, wherein the apparatus is further configured to:
   generate a final score based on the standard value, the extended value, and the patient complexity adjustment; and
   determine the EEDVL using the final score and a threshold table, wherein the threshold table comprises a set of thresholds ranges corresponding to a set of emergency department visit levels, wherein the final score is within a particular threshold range of the set of threshold ranges, and wherein the EEDVL comprises the emergency department visit level corresponding to the particular threshold range.

9. A non-transitory computer-readable storage medium for deriving an expected emergency department visit level (EEDVL), the EEDVL comprising an expected medical claims coding level, the non-transitory computer-readable storage medium storing program code instructions that, when executed, cause a healthcare claim payer computing device to:
   receive a set of healthcare claims for a patient's visit to an emergency department, wherein the set of healthcare claims comprises a claimed emergency department visit level (CEDVL), the CEDLV comprising a claimed medical claims coding level;
   extract, from the set of healthcare claims, a set of treatment codes indicative of (a) services performed during the patient's visit to the emergency department, and (b) one or more conditions associated with the patient's visit to the emergency department;
   derive a standard value by:
      automatically identifying, based at least in part on the set of treatment codes, data indicative of one or more reasons for the patient's visit to the emergency department,
      automatically determining, based at least in part on the one or more reasons for the patient's visit to the emergency department and using a standard value lookup table, a patient complexity adjustment (PSCA) score for each of the one or more reasons for the patient's visit,
      automatically deriving, based at least in part on the PSCA score, the standard value for the patient's visit to the emergency department, wherein the standard value comprises a standard resource valuation;

derive, based at least in part on the set of treatment codes, an extended value indicative of resource utilization during the patient's visit to the emergency department;

derive, based at least in part on the set of treatment codes, a patient complexity adjustment by:
    automatically identifying, based at least in part on the set of treatment codes, one or more secondary codes for the patient's visit to the emergency department,
    automatically determining, using a patient complexity adjustment lookup table, a secondary score based at least in part on the one or more secondary codes, and
    automatically deriving, based at least in part on the secondary score, the patient complexity adjustment;

determine the EEDVL, based at least in part on the standard value, the extended value, and the patient complexity adjustment;

compare the CEDVL and the EEDVL to determine if the CEDVL and the EEDVL are different; and responsive to a determination that the CEDVL and the EEDVL are different, automatically (a) generate a notification comprising the CEDVL and the EEDVL, and (b) automatically transmit the notification to a user account associated with the CEDVL.

10. The method of claim 1, further comprising:
determining a payout for the healthcare claims using the EEDVL; and
transmitting a payment to the healthcare provider based on the determined payout.

11. The apparatus of claim 5, further comprising an adjudication module configured to:
determine a payout for the healthcare claims using the EEDVL; and
transmit a payment to the healthcare provider based on the determined payout.

* * * * *